United States Patent
Chrzan et al.

(10) Patent No.: US 8,053,728 B2
(45) Date of Patent: Nov. 8, 2011

(54) GAS SENSOR WITH AN ESPECIALLY EXPLOSION-PROOF HOUSING

(75) Inventors: Rigobert Chrzan, Bad Oldesloe (DE); Andreas Moldt, Lübeck (DE); Thomas Wiedemann, Pölitz (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 980 days.

(21) Appl. No.: 11/968,926

(22) Filed: Jan. 3, 2008

(65) Prior Publication Data

US 2010/0283991 A1 Nov. 11, 2010

(30) Foreign Application Priority Data

Mar. 10, 2007 (DE) .......................... 10 2007 011 750

(51) Int. Cl.
 *G01J 5/00* (2006.01)
(52) U.S. Cl. ................................... 250/338.1
(58) Field of Classification Search ................ 250/338.1
 See application file for complete search history.

(56) References Cited

U.S. PATENT DOCUMENTS

| 4,850,669 A * | 7/1989 | Welker et al. ................ 385/75 |
| 5,923,035 A | 7/1999 | Winkler et al. |
| 2005/0127297 A1 * | 6/2005 | Starta et al. ................ 250/341.5 |
| 2007/0192041 A1 * | 8/2007 | Goldstein et al. ................ 702/24 |

FOREIGN PATENT DOCUMENTS

| DE | 197 13 928 C1 | 4/1998 |
| JP | 8184556 | 7/1996 |

* cited by examiner

*Primary Examiner* — David Porta
*Assistant Examiner* — Christine Sung
(74) *Attorney, Agent, or Firm* — McGlew and Tuttle, P.C.

(57) ABSTRACT

A gas sensor with a housing (1, 11) has an optical signal transmission to the environment of the gas sensor (10). At least one light-emitting diode (3) is arranged in the housing (1, 11) on the inner side of a disk (4) that is transparent to light. At least one optical light guide (5), for coupling in the light of the light-emitting diode (3), is arranged in the housing (1, 11) on the outer side of the disk (4) that is transparent to light. The optical light guide (5) extends up to the outer surface (6) of the housing (1, 11).

20 Claims, 2 Drawing Sheets

GAS SENSOR WITH AN ESPECIALLY EXPLOSION-PROOF HOUSING

CROSS REFERENCE TO RELATED APPLICATIONS

This application claims the benefit of priority under 35 U.S.C. §119 of German Patent Application DE 10 2007 011 750.9 filed Mar. 10, 2007, the entire contents of which are incorporated herein by reference.

FIELD OF THE INVENTION

The present invention pertains to a gas sensor with an especially explosion-proof housing.

BACKGROUND OF THE INVENTION

Such gas sensors are used typically for determining the concentrations of explosive gases or gas mixtures in an environment and are based, in general, on measurements with so-called heat evolution sensors or on infrared optical absorption measurements with a radiation source and with at least one measuring detector. A prior-art infrared sensor with a measuring section outside the sensor housing, in the environment containing the gas to be measured, appears from DE 197 13 928 C1.

Explosion-proof gas sensors are subject to the requirements of explosion protection, and a pressure-proof encapsulation of the housing may be additionally necessary. The optical and electronic components necessary for the measurement, i.e., the measuring module, which may lead to ignition of a combustible gas without special protection, are accommodated in a special housing, which meets the requirements imposed on the particular type of protection required.

The interface to the environment is via at least one duct of a pressure-proof design for the electrical cable leads.

Outside the housing encapsulated in a pressure-proof manner, the measuring space is in an environment that is accessible to the gas to be measured, which may possibly be explosive, i.e., the measured gas sample holder.

Based on the requirements for approval concerning explosion protection, the cable ducts are of a very complicated design and therefore cost-intensive. In addition to this are the extensive and likewise cost-intensive tests associated with the approval.

SUMMARY OF THE INVENTION

The object of the present invention is therefore to provide a gas sensor with an explosion-proof housing, which makes possible the transmission and the display of optically displayed operating states to the environment without a complicated and cost-intensive additional pressure-proof duct through the sensor housing being necessary.

According to the invention, a gas sensor is provided comprising a housing with an outer surface and an optical signal transmission means for transmission of an optical signal to the environment of the gas sensor. The optical signal transmission means includes a disk that is transparent to light and a light-emitting diode arranged in the housing on an inner side of the disk, and an optical light guide for coupling in the light of the light-emitting diode. The light guide is arranged in the housing on an outer side of the disk, the optical light guide extending up to the outer surface of the housing.

The light-emitting diode is part of an infrared transceiver, which is used for the bidirectional optical data transmission and contains a photocell acting as a detector. The light-emitting diode may emit in the visible wavelength range. The gas sensor may be an optical infrared sensor.

The gas sensor may be part of a gas sensor system that further comprises an analysis unit with another infrared transceiver for coupling in and/or out light for control and/or measured data. The analysis unit is arranged outside of the outer surface of the housing.

The gas sensor also comprises a tilted mirror arranged at the housing for deflecting the measured beam exiting and entering through the infrared-transparent disk. The optical light guide extends outwardly, towards opposite outer surfaces of the housing.

The optical light guide may consist essentially of one of polymethacrylate (PMMA) and polycarbonate (PC). The disk that is transparent to light may consist of sapphire. The gas sensor may be provided for measuring explosive hydrocarbons or gas mixtures containing hydrocarbons.

According to another aspect of the invention, a gas sensor system is provided including a housing with an outer surface, an infrared transceiver including a radiation source and an absorption measuring section and an optical signal transmission means for transmission of an optical signal to the environment of the gas sensor. The optical signal transmission means includes an optical light guide and a disk that is transparent to light. The radiation source is arranged in the housing on an inner side of the disk. The optical light guide is for coupling in the light of the radiation source. The light guide is arranged in the housing on an outer side of the disk. The optical light guide extends from a location of coupling in the light of the radiation source up to the outer surface of the housing. A measuring path deflection mirror is arranged on an outer side of the disk and provides a measuring path from the radiation source to the deflection mirror and from the deflection mirror to the absorption measuring section for the concentration measurement of the gas to be measured in the environment of the gas sensor.

According to another aspect of the invention, a method is provided for measuring gas in the environment of a gas sensor. The method includes providing the gas sensor with a housing with an outer surface and providing the gas sensor with an infrared transceiver including a radiation source and an absorption measuring section. An optical signal transmission means for transmission of an optical signal to the environment of the gas sensor is provided wherein the optical signal transmission means includes an optical light guide and a disk that is transparent to light. The radiation source is arranged in the housing on an inner side of the disk. The light guide is arranged in the housing on an outer side of the disk. The optical light guide extends from a location of coupling in the light of the radiation source up to the outer surface of the housing. The optical light guide is used for coupling in the light of the radiation source and transmitting the coupled in light to provide the optical signal to the environment of the gas sensor. The sensor is also provided with a measuring path deflection mirror arranged on an outer side of the disk and providing a measuring path from the radiation source to the deflection mirror and from the deflection mirror to the absorption measuring section for the concentration measurement of the gas to be measured in the environment of the gas sensor. The infrared transceiver, the measuring path and the measuring path deflection mirror are used to determine concentrations of gases or gas mixtures in the environment of the gas sensor.

The method advantageously may include providing an analysis unit with another infrared transceiver for coupling in and/or out radiation. The analysis unit may be arranged outside of the outer surface of the housing. The infrared transceiver of the gas sensor is then used for bidirectional optical data transmission with the analysis unit and receiving control and/or measured data at the analysis unit from the light of the radiation source transmitted as an optical signal to the environment of the gas sensor. The radiation source may comprise a light-emitting diode arranged in the housing on an inner side of the disk and the absorption measuring section may comprise a photocell acting as a detector.

It is especially advantageous for the determination of concentrations of gases or gas mixtures in the environment of the gas sensor to comprise a determination of concentrations of explosive hydrocarbons or gas mixtures containing hydrocarbons.

An exemplary embodiment of the present invention will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
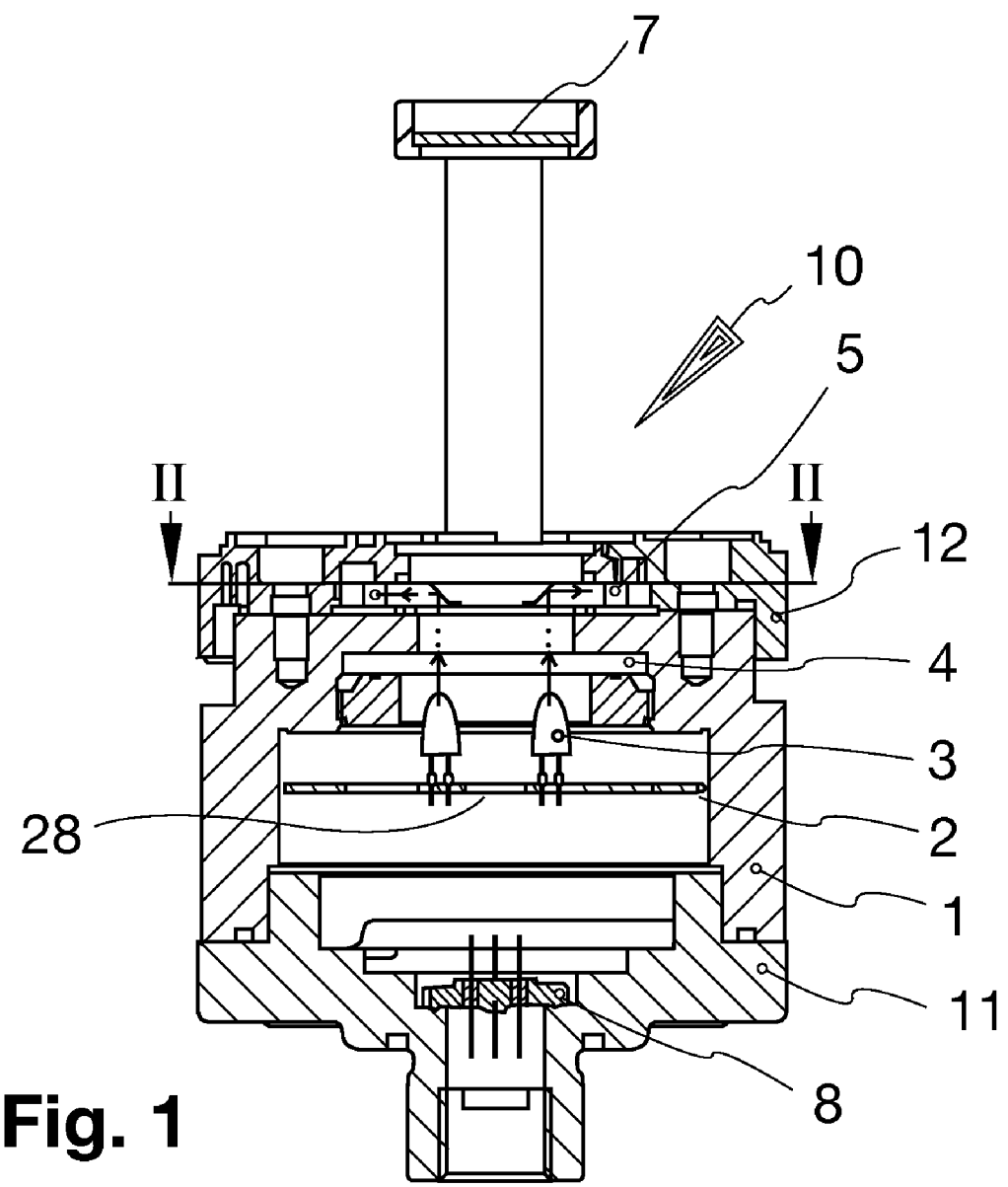
FIG. 1 is a longitudinal sectional view through a gas sensor.

Referring to the drawings in particular FIG. 1 shows a section through the infrared optical gas sensor 10 with the explosion-proof housing 1, 11 encapsulated in a pressure-proof manner, which is made, for example, of steel.

Two light-emitting diodes (LEDs) 3 are located on a printed circuit board of the measuring module 2 as radiation sources, for example, a yellow LED and a green LED in a 5-mm round housing. The measuring module 2 and LEDs 3 are part of an infrared transceiver. The LEDs have a rather small radiation angle of, e.g., plus/minus 15° and have a luminous density of several candela. The light of the light-emitting diodes 3 is coupled through a disk or window 4, which is designed as a sapphire disk and is also transparent to infrared light for the measuring beam, into the optical light guide 5, which is beveled at an angle of about 45° and is made of polymethyl methacrylate (PMMA) or polycarbonate (PC). The path of the light to light emitting locations 6 on the outer surface of the housing 1, 11 is indicated by arrows.

The measuring beam for the concentration measurement proper of the gas to be measured in the environment of the gas sensor 10 exits through the disk or window 4 and is deflected by means of a tilted mirror 7 and sent back again through the disk 4. The measuring module 2 has an absorption measuring section 28 suitable for the measurement. The absorption measuring section 28 has a photocell acting as a radiation detector. Reference is made in this connection, for example, to DE 197 13 928 C1 with the corresponding description and U.S. Pat. No. 5,923,035 which is hereby incorporated by reference in its entirety.

The optical light guides 5 are arranged, for example, bonded in a cover 12 connected to the upper part of the housing 1. The tilted mirror 7 is fastened to the upper part of the housing 1 or is designed as an assembly unit, especially as an injection-molded part.

The electric terminals are led in via explosion-proof cable leads 8 of a complicated pressure-proof design.

Figure 2:
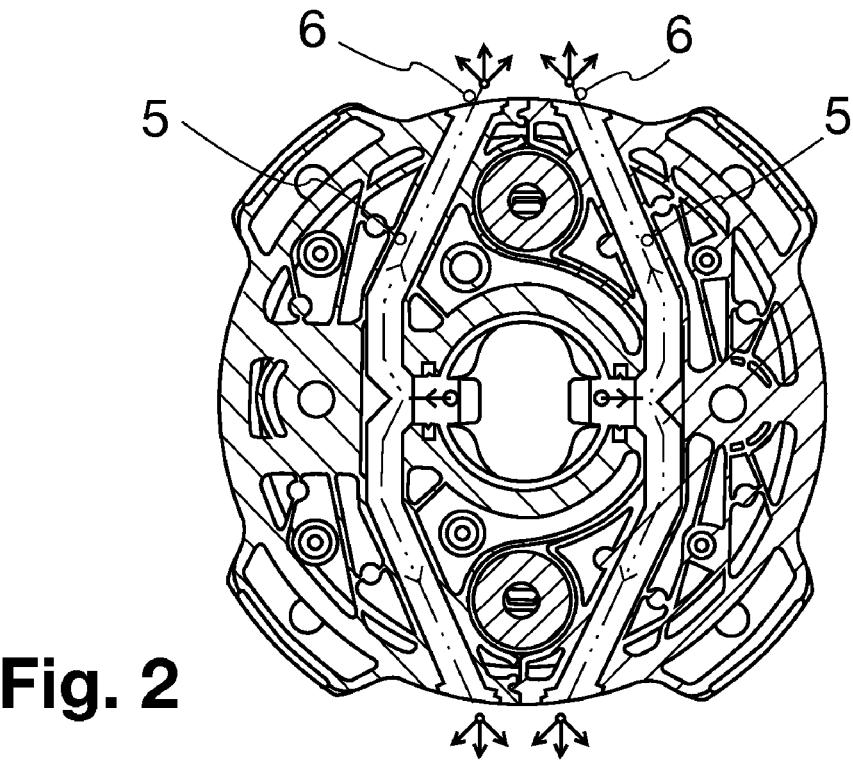
FIG. 2 is a sectional view taken at right angles through FIG. 1 along the line labeled H-H.
Figure 3:
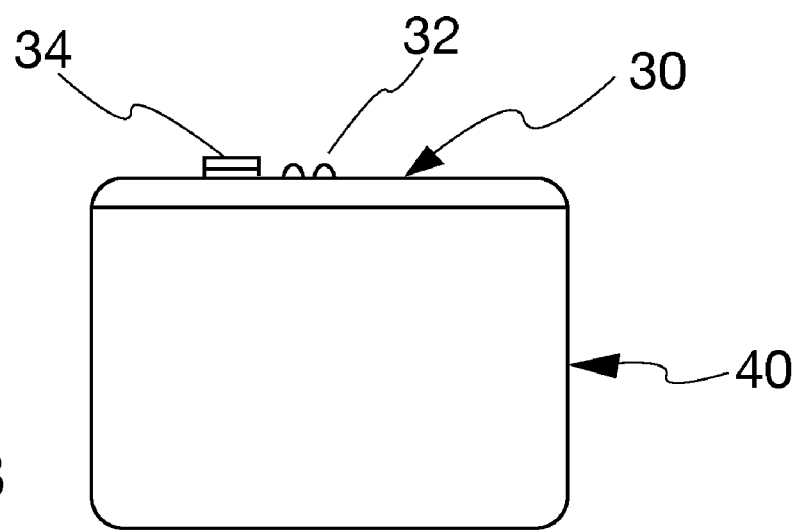
FIG. 3 is a schematic view of an external analysis unit.

FIG. 2 shows a section through the symmetrically designed optical light guide 5. The optical light guide 5 is designed such that the light of the light-emitting diodes 3 is coupled out for better visibility in the environment on both sides of the gas sensor 10. The total of four light exit surfaces for good external perceptibility corresponding to the outer surfaces 6 are preferably of a structured design for the purpose of better visibility.

The arrangement shown offers the possibility of achieving bidirectional data transmission by means of an (external) infrared transceiver 30. Such an infrared transceiver 30 is provided externally of the gas sensor 10 for communication (bidirectional data transmission) with the gas sensor 10. Such infrared transceivers 30 comprise, among other things, a diode 32 emitting in the infrared range (IRED) and a photocell 34, which is designed especially as a photodiode and which acts as a detector. The coupling out and coupling in of the digital optical signals of the infrared transceiver 30 take place analogously to the coupling out of the light of the light-emitting diodes 3. For example, status information and measured data can be read out by means of an external analysis unit 40 (associated with or connected with the external infrared transceiver 30) by means of such an optical data transmission. The analysis unit 40 is now to be directed towards the light exit surfaces such that there is an optical connection between the infrared transceiver 30 of the analysis unit 40 and the light exit surfaces of the optical light guide 5. There is also a direct optical connection to the complementary infrared transceiver (the absorption measuring section suitable for the measurement and associated or part of the measuring module 2) in the gas sensor 10.

The explosion-proof gas sensor 10 is used especially to measure the concentrations of explosive gases or gas mixtures also with air, especially of hydrocarbons or gas mixtures containing hydrocarbons.

While a specific embodiment of the invention has been shown and described in detail to illustrate the application of the principles of the invention, it will be understood that the invention may be embodied otherwise without departing from such principles.

What is claimed is:

1. A gas sensor comprising:
a housing with an outer surface;
an optical signal transmission means for transmission of an optical signal to the environment of the gas sensor, said optical signal transmission means including a disk that is transparent to light and a light-emitting diode arranged in said housing on an inner side of said disk, and an optical light guide for coupling in the light of said light-emitting diode, said light guide being arranged in said housing on an outer side of said disk, said optical light guide extending up to a plurality of spaced light emitting locations on said outer surface of said housing.

2. A gas sensor in accordance with claim 1, wherein said light-emitting diode is part of an infrared transceiver, which is used for bidirectional optical data transmission and contains a photocell acting as a detector.

3. A gas sensor in accordance with claim 1, wherein said light-emitting diode emits radiation in the visible wavelength range.

4. A gas sensor in accordance with claim 2, further comprising an analysis unit with another infrared transceiver for coupling in and/or out light for control and/or measured data, said analysis unit being arranged outside of said outer surface of said housing.

5. A gas sensor in accordance with claim 1, wherein said gas sensor is an optical infrared sensor.

6. A gas sensor in accordance with claim 4, further comprising a tilted mirror arranged at said housing for deflecting the measured beam exiting and entering through said infrared-transparent disk.

7. A gas sensor in accordance with claim 1, wherein said optical light guide extends to said light emitting locations on diametrically opposite sides of said outer surface of said housing.

8. A gas sensor in accordance with claim 1, wherein said optical light guide consists essentially of one of polymethacrylate (PMMA) and polycarbonate (PC).

9. A gas sensor in accordance with claim 1, wherein said disk that is transparent to light consists of sapphire.

10. A gas sensor in accordance with claim 1, wherein said gas sensor is for measuring explosive hydrocarbons or gas mixtures containing hydrocarbons.

11. A method of measuring gas in the environment of a gas sensor, the method comprising the steps of:
    providing the gas sensor with a housing with an outer surface;
    providing the gas sensor with an infrared transceiver including a radiation source and an absorption measuring section;
    providing an optical signal transmission means for transmission of an optical signal to the environment of said gas sensor, said optical signal transmission means including an optical light guide and a disk that is transparent to light;
    arranging said radiation source in said housing on an inner side of said disk;
    arranging said light guide in said housing on an outer side of said disk, said optical light guide extending from a location of coupling in the light of said radiation source up to said outer surface of said housing;
    using said optical light guide for coupling in the light of said radiation source and transmitting the coupled in light to provide the optical signal to the environment of said gas sensor;
    providing a measuring path deflection mirror arranged on an outer side of said disk and providing a measuring path from said radiation source to said deflection mirror and from said deflection mirror to said absorption measuring section for the concentration measurement of the gas to be measured in the environment of the gas sensor;
    using the infrared transceiver, the measuring path and the measuring path deflection mirror to determine concentrations of gases or gas mixtures in the environment of the gas sensor;
    providing an analysis unit with another infrared transceiver for coupling radiation in and out of said analysis unit, said analysis unit being arranged at a location outside of said outer surface of said housing;
    using said infrared transceiver of the gas sensor for bidirectional optical data transmission with said analysis unit, and receiving control and/or measured data at said analysis unit from the light of said radiation source transmitted as an optical signal to the environment of said gas sensor.

12. A method of measuring gas in the environment of a gas sensor in accordance with claim 11, wherein:
    said light guide is arranged to convey the radiation from said radiation source to a plurality of light emitting locations spaced from each other on said outer surface of said housing, and emitting radiation from said plurality of light emitting locations in a plurality of different directions.

13. A gas sensor system comprising:
    a housing with an outer surface;
    a radiation source arranged in said housing to transmit radiation;
    a radiation detector arranged in said housing to detect radiation;
    an optical system mounted on said housing, and conveying the radiation from said radiation source to a plurality of light emitting locations on said outer surface of said housing, said plurality of light emitting locations on said outer surface being spaced from each other on said outer surface, said optical system emitting the radiation from said spaced locations in different directions from said housing;
    said optical system including a measuring path arranged to direct the radiation from one of said light emitting locations, through a gaseous environment outside said housing, and then back to said radiation detector in said housing;
    said optical system including an optical light guide conveying the radiation from said radiation source to another of said light emitting locations.

14. A gas sensor system in accordance with claim 13, wherein said radiation source comprises a light-emitting diode arranged in said housing and said radiation detector comprises a photocell.

15. A gas sensor system in accordance with claim 14, wherein said light-emitting diode emits radiation in the visible wavelength range, and the gas sensor is an optical infrared sensor.

16. A gas sensor system in accordance with claim 14, wherein said optical light guide consists essentially of one of polymethacrylate (PMMA) and polycarbonate (PC).

17. A gas sensor system in accordance with claim 13, wherein:
    said housing and said optical system provide an explosion proof container around said radiation source and said radiation detector.

18. A gas sensor system in accordance with claim 13, further comprising:
    a measuring module arranged in said housing and connected to both said radiation source and said radiation detector to measure a gas concentration along said measuring path;
    said measuring module also forming a bidirectional optical data transceiver with said radiation source, said radiation detector, and said optical system to optically and bidirectionally transferring data into and out of said housing though one of said light emitting locations.

19. A gas sensor system in accordance with claim 18, further comprising:
    an analysis unit arranged outside said outer surface of said housing, said analysis unit including another bidirectional optical data transceiver for optically and bidirectionally transfer the data with said bidirectional optical data transceiver in said housing.

20. A gas sensor system in accordance with claim 13, wherein:
    said light guide conveys the radiation to still another of said light emitting locations, said another light emitting location and said still another light emitting location being arranged on diametrically opposite sides of said housing.

* * * * *